(12) United States Patent
Yamashita

(10) Patent No.: US 7,223,847 B2
(45) Date of Patent: May 29, 2007

(54) METHOD FOR PRODUCING COBALT-PROTEIN COMPLEX

(75) Inventor: Ichiro Yamashita, Nara (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 456 days.

(21) Appl. No.: 10/644,774

(22) Filed: Aug. 21, 2003

(65) Prior Publication Data

US 2004/0158047 A1    Aug. 12, 2004

Related U.S. Application Data

(63) Continuation of application No. PCT/JP02/10127, filed on Sep. 27, 2002.

(30) Foreign Application Priority Data

Oct. 1, 2001    (JP) .............................. 2001-305273

(51) Int. Cl.
 *C07K 1/00* (2006.01)
 *A61B 5/055* (2006.01)
(52) U.S. Cl. ...................... 530/400; 530/350; 424/9.34
(58) Field of Classification Search ................ 530/400, 530/350; 424/9.34
 See application file for complete search history.

(56) References Cited

U.S. PATENT DOCUMENTS 5,358,722 A    10/1994 Monzyk 6,180,389 B1    1/2001 Douglas et al.

FOREIGN PATENT DOCUMENTS

WO    WO 2004/033366 A1    4/2004

OTHER PUBLICATIONS

Douglas et al., Inorg. Chem., vol. 39, pp. 1828-1830, 2000.*
Yang et al., Biochem. J., vol. 338, pp. 615-618, 1999.*
Matias et al., Acta Cryst. vol. F67, pp. 503-506, 2005.*
Okuda, M. et al "Fabrication of Nickel and Chromium Nanoparticles using the Protein Cage of Apoferritin", Biotechnology and Bioengineering Including: Symposium Biotechnology in Energy Production and Conservation, vol. 84, No. 2, Oct. 20, 2003, pp. 187-194, (XP-002975877).
Allen, M. et al, "Constrained Synthesis if Cobalt Nanomaterials in the 12-Subunit Protein Cage from *Listeria innocua*", Inorganic Chemistry, vol. 42, No. 20, Oct. 6, 2003, pp. 6300-6305, (XP-002301238).
D'Souza, V. M. et al., "Divalent Metal Binding Properties of the Methionly Aminopeptidase from *Escherichia coli*", Biochemistry, vol. 39, No. 13, Apr. 4, 2000, pp. 3817-3826, (XP-002301239).

* cited by examiner

*Primary Examiner*—Jon Weber
*Assistant Examiner*—Abdel A. Mohamed
(74) *Attorney, Agent, or Firm*—McDermott Will & Emery LLP

(57) ABSTRACT

A method for obtaining a cobalt-apoferritin complex according to the present invention includes: the step a) of preparing a solution including a $Co^{2+}$ ion, a protein, a pH buffer agent and a $Co^{2+}$ associating agent; and the step b) of adding an oxidizing agent to the solution and thereby making the protein contain a fine particle including cobalt.

6 Claims, 8 Drawing Sheets

METHOD FOR PRODUCING COBALT-PROTEIN COMPLEX

CROSS-REFERENCE TO RELATED APPLICATION

This is a continuation of International Patent Application PCT/JP02/10127, filed Sep. 27, 2002.

BACKGROUND OF THE INVENTION

The present invention relates to a method for producing particles, and more particularly related to a method for producing a cobalt-protein complex containing a cobalt particle and its related technologies.

In recent years, there have been vigorous studies in the field of bioelectronics which is a combination of biotechnology and electronics. As a result of such studies, biosensors using proteins such as enzymes, or like devices have been already practically used.

As an attempt of the application of biotechnology to other fields, there is a study of incorporating particles composed of a metal or a metal compound into apoferritin which is a protein having the function of holding a metal compound, thereby producing particles having a uniform diameter at the nano-order level. In order to introduce various kinds of metals, metal compounds or the like into apoferritin according to various applications, many researches have been carried out.

Hereinafter, description of apoferritin will be given. Apoferritin is a protein which is extensively present in the biological world. It has the function of adjusting the amount of iron which is a necessary micronutrient element in a living body. A complex of iron or an iron compound with apoferritin is called "ferritin". When the amount of iron exceeds a necessary level in a living body, iron could be harmful. So, excessive iron is stored in a living body in the form of ferritin. Ferritin releases iron ions, when necessary, and then it becomes apoferritin again.

FIG. 1 is a schematic view of the structure of apoferritin. As shown in FIG. 1, apoferritin 1 is a globular protein in which 24 monomer subunits each being composed of a polypeptide chain assemble and form non-covalent bonds and which has a molecular weight of about 460,000. The globular protein has a diameter of about 12 nm and exhibits higher thermal stability and higher pH stability than normal proteins. The apoferritin 1 has a hollow-like holding portion 4 having a diameter of about 6 nm in the center. The holding portion 4 is connected to the outside via a channel 3. For example, when ferric iron ions are incorporated into the apoferritin 1, the iron ions enter the apoferritin 1 through the channel 3 and are oxidized in a portion called the ferrooxidase center in one of the subunits. Then, they reach the holding portion 4 and finally are condensed in a negative charge region located in the inside surface of the holding portion 4. Then, 3000-4000 iron atoms assemble and are held in the holding portion 4 in the crystalline form of ferrihydride ($5Fe_2O_3.9H_2O$). A particle containing metal atoms held in the holding portion 4 has the almost same diameter as that of the holding portion 4, i.e., about 6 nm.

Using apoferritin, a complex of apoferritin with particles artificially made to contain a metal other than iron or a metal compound is produced.

Up until today, there have been reports of introductions of metals or metal compounds into apoferritin, such as introduction of manganese into apoferritin (P. Mackle, 1993, J. Amer. Chem. Soc. 115, 8471-8472; F. C. Meldrum et al., 1995, J. Inorg. Biochem. 58, 59-68), introduction of uranium into apoferritin (J. F. Hainfeld, 1992, Proc. Natl. Acad. Sci. USA 89, 11064-11068), introduction of beryllium into apoferritin (D. J. Price, 1983, J. Biol. Chem. 258, 10873-10880), introduction of aluminum into apoferritin (J. Fleming, 1987, Proc. Natl. Acad. Sci. USA, 84, 7866-7870), and introduction of zinc into apoferritin (D. Price and J. G. Joshi, Proc. Natl. Acd. Sci. USA, 1982, 79, 3116-3119). Particles composed of any one of these metals or metal compounds have also about the same diameter as that of the holding portion 4 of apoferritin, i.e., about 6 nm.

Processes by which a particle containing iron atoms is formed in the natural world will be briefly described hereinafter.

On the surface of the channel 3 (see FIG. 1) connecting the outside and inside of the apoferritin 1, amino acid residues with a negative charge at pH 7-8 are exposed and $Fe^{2+}$ ions with a positive charge are incorporated into the channel 3 through electrostatic interaction.

Also, on the inside surface of the holding portion 4 of the apoferritin 1, many glutamic acid residues which are amino acid residues and have a negative charge at pH 7-8 are exposed as on the inside surface of the channel 3. $Fe^{2+}$ ions incorporated through the channel 3 are oxidized at the ferroxidase center and then are introduced to the holding portion 4 located at the inside of the apoferritin 1. Iron ions are condensed through electrostatic interaction, and then nucleation of ferrihydride ($5Fe_2O_3.9H_2O$) crystals occurs.

Thereafter, increasingly incorporated iron ions are adhered to the nucleus of a ferrihydride crystal and the nucleus composed of iron oxide is grown. Thus, particles with a diameter of 6 nm are formed in the holding portion 4. This is how iron ions are incorporated and particles composed of iron oxide is formed.

The mechanism of incorporation of iron ions into apoferritin has been described. However, since ions of any other metals which have been reported regarding introduction thereof into apoferritin have a positive charge, ions are incorporated into apoferritin by almost the same mechanism as that for iron ions.

SUMMARY OF THE INVENTION

As for introduction of cobalt into apoferritin, Douglas et al. have reported introduction of cobalt hydroxide (CoO(OH)) (T. Douglas and V. T. Stark, "Nanophase Cobalt Oxyhydroxide Mineral Synthesizer within the Protein Cage of Ferritin", Inorg. Chem., 39, 2000, 1828-1830). With the method reported by Douglas et al., a cobalt-apoferritin complex containing a cobalt particle can be produced.

In the method of Douglas, however, no buffer solution is used and thus the pH of a solution in which a cobalt-apoferritin complex containing a cobalt particle is formed can be changed (reduced). Specifically, if the solution is left to stand for a few days, some of the cobalt particles contained therein are eluted into the solution. This makes it difficult to maintain the diameter of each cobalt particle contained therein at the diameter thereof before the operations. Therefore, it is difficult to obtain a cobalt-apoferritin complex containing a cobalt particle having a uniform diameter.

To solve the above-described problems, the present invention has been devised, and it is therefore an object of the present invention to provide a method for obtaining a cobalt-protein complex containing a cobalt particle having a uniform diameter.

A method for producing a cobalt-protein complex according to the present invention includes: the step a) of preparing a solution containing $Co^{2+}$ ions, a protein, a pH buffer agent and a $Co^{2+}$ associating agent; and the step b) of adding an oxidizing agent to the solution and thereby making the protein contain particles composed of cobalt.

With a $Co^{2+}$ associating agent, $Co^{2+}$ ions are condensed in the inside of a protein. Thus, a reaction of the $Co^{2+}$ ions and an oxidizing agent is preferentially occurs. At this time, by adjusting the pH of a solution to a desired level using a pH buffer agent, the reaction of the $Co^{2+}$ ions and the oxidizing agent is prevented from proceeding in the reverse direction, and thus elution of cobalt particles contained in the protein can be prevented. Accordingly, a cobalt-protein complex containing a cobalt particle having a uniform diameter can be obtained.

It is preferable that each of the pH buffer agent and the $Co^{2+}$ associating agent is HEPES.

HEPES has functions as a pH buffer agent and the $Co^{2+}$ associating agent. Therefore, it is not necessary to prepare a pH buffer agent and a $Co^{2+}$ associating agent separately.

The protein may be apoferritin.

The oxidizing agent may be $H_2O_2$.

Another method for producing a cobalt-protein complex includes: the step a) of preparing a solution containing $Co^{2+}$ ions, apoferritin and HEPES; and the step b) of adding $H_2O_2$ to the solution and thereby making the apoferritin contain particles composed of cobalt.

According to the present invention, a reaction of $Co^{2+}$ ions and $H_2O_2$ occurs in a HEPES solution. Thus, the pH of the solution is constant and elution of cobalt particles contained in apoferritin can be prevented. Accordingly, a cobalt-protein complex containing a cobalt particle having a uniform diameter can be obtained.

DESCRIPTION OF THE PREFERRED EMBODIMENTS

In the method of Douglas et al., a reaction represented by the following chemical reaction formula 1 is utilized.

[Formula 1]

Figure 1:
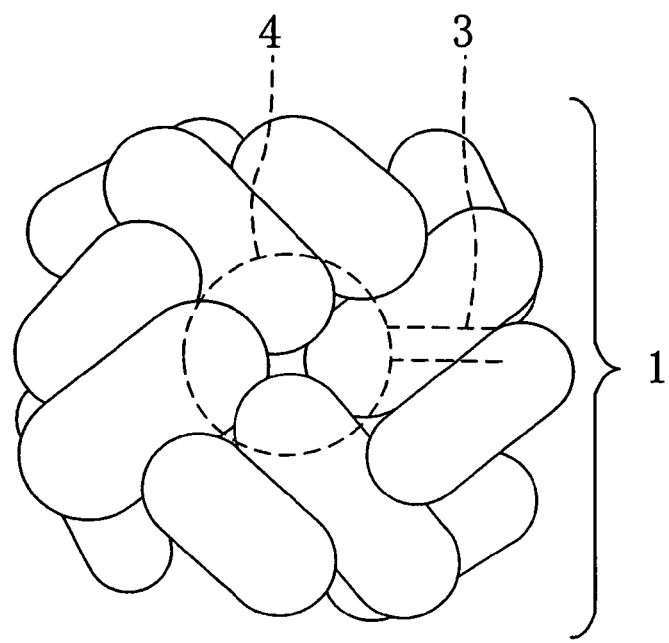
FIG. 1 is a schematic illustration of the structure of apoferritin.

As can be understood from the chemical reaction formula 1, as a reaction proceeds, the acidity of a reaction solution is increased. When the reaction solution is at around pH 8, many amino acid residues with a negative charge are exposed on the inside surface of a holding portion 4 of apoferritin 1 shown in FIG. 1, and thus $Co^{2+}$ ions are introduced into the holding portion 4. Because of this, particles of cobalt hydroxide are easily formed in the holding portion 4 of the apoferritin 1. Accordingly, with the pH of the reaction solution kept at around 8, $H^+$ which is generated as the reaction proceeds is neutralized. Therefore, in the method of Douglas et al., NaOH is added thereto dropwise to control the pH of the apoferritin solution while a cobalt nitrate solution and a hydrogen peroxide solution are gradually added to an apoferritin solution by a very small amount at a time and the solution is briskly stirred by a stirrer.

As has been described, in the method of Douglas et al., it is difficult to keep the diameter of cobalt particles at the diameter thereof before the operations when forming a cobalt-apoferritin complex. The present inventors, therefore, re-examined the method of Douglas et al. to find the following problems.

A first problem is in that pH is controlled by not using a buffer solution but by dropping NaOH to an apoferritin solution. The NaOH concentration abruptly rises in part of the apoferritin solution to which NaOH is dropped, locally, and then pH is increased. Therefore, the function of controlling pH may not be sufficient. Therefore, the direction of the chemical reaction represented by the reaction formula 1 may be reversed, resulting in elution of cobalt particles contained in cobalt-apoferritin complexes into the solution.

A second problem is in that NaOH is used. NaOH is a strong protein denaturant. The NaOH concentration abruptly rises in part of the apoferritin solution to which NaOH is dropped, locally, and therefore apoferritin may be denatured. Accordingly, apoferritin may be in the state where it can not fully exhibit its original characteristics. In other words, apoferritin may not be able to fully hold cobalt particles.

A third problem is in that it is difficult to perform the method on an industrial scale. In the method of Douglas et al., NaOH is dropped to the apoferritin solution to control the pH thereof while a cobalt nitrate solution and a hydrogen peroxide solution are gradually added to an apoferritin solution by a very small amount at a time. In this method, when the total amount of the reaction solution is about 20-50 ml, the chemical reaction can be easily led. However, if a reaction scale is enlarged to an industrial level, it will require a huge amount of time to add cobalt nitrate, a hydrogen peroxide solution and NaOH to an apoferritin solution. Moreover, it will be also difficult to uniformly diffuse cobalt nitrate, a hydrogen peroxide solution, and NaOH in a large amount of apoferritin solution. Therefore, the method is considered to be not practical.

Embodiment 1

An embodiment of the present invention to be described hereinafter has been devised on the basis of the above-described examination. A method for producing a cobalt-apoferritin complex according to this embodiment will be described with reference to FIGS. 1 through 3.

Figure 2:
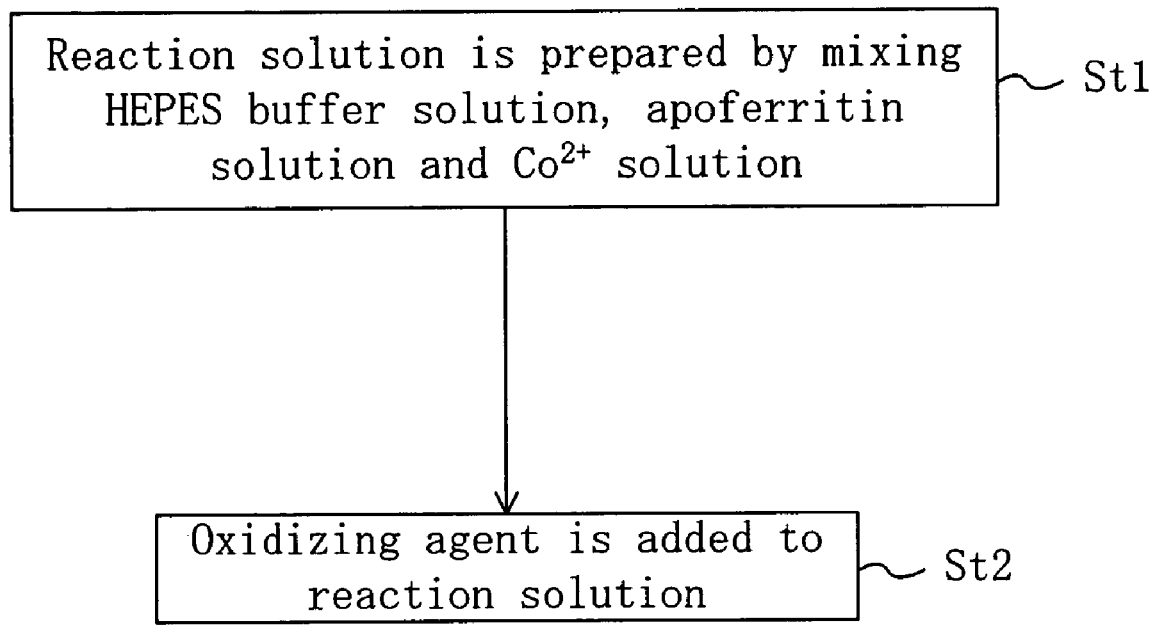
FIG. 2 is a flowchart illustrating a method for producing a cobalt-apoferitin complex according to Embodiment 1.

FIG. 2 is a flowchart illustrating a method for producing a cobalt-apoferitin complex according to this embodiment.

First, in Step St1, a reaction solution is prepared by mixing a HEPES buffer solution, an apoferritin solution and $Co^{2+}$ ion solution (e.g., a cobalt nitrate solution) in this order, as shown in FIG. 2.

Next, in Step St2, an oxidizing agent (e.g., $H_2O_2$) is added to the reaction solution, as shown in FIG. 2. By this operation, cobalt hydroxide (CoO(OH)) is introduced into the holding portion 4 of the apoferritin 1 and then cobalt-apoferritin complexes are generated, as shown in FIG. 2.

Note that all of the above-described operations for producing a cobalt-apoferritin complex are performed at room temperature or in a temperature range in which a protein is not denatured, while the solution is stirred by a stirrer.

Next, detail description for each of the steps will be given.

First, in Step St1, the pH of the reaction solution is adjusted to be in a range from about 7.5 to 9.0. More specifically, the pH of the reaction solution is preferably adjusted to be in a range from about 8.0 to 8.8. When the pH of the reaction solution is in a range from about 8.0 to 8.8, many amino acid residues with a negative charge are exposed on the inside surface of the holding portion 4 of the apoferritin 1 and thus $Co^{2+}$ ions are led to the holding portion 4. Therefore, particles composed of cobalt hydroxide (CoO(OH)) can be easily formed in the holding portion 4 of the apoferritin 1. The state of cobalt particles formed at each pH is shown in Table 1.

and then cobalt-apoferritin complexes may be caught by the precipitates. Accordingly, a recovery rate of cobalt-apoferritin complexes may be reduced.

For example, when the apoferritin concentration is 0.5 mg/ml (about 1 μM), $Co^{2+}$ ions are added at a concentration of 2-3 mM. Although any compound may be used to add $Co^{2+}$ ions, it is particularly preferable to use cobalt ammonium sulfate or cobalt nitrate. If cobalt ammonium sulfate or cobalt nitrate is used, $Co^{2+}$-HEPES associated pairs which will be described later can be easily formed and a reaction will not proceed rapidly (i.e. mixed substances will not react explosively).

Note that in this embodiment, the reaction solution is prepared so that the final concentration of HEPES is 30 mM (pH 8.8), the final concentration of apoferritin is 0.5 mg/ml (1 μM), and the final concentration of $Co^{2+}$ ion is 5 mM in Step St1.

In the Step St2, a hydrogen peroxide solution of 0.01-3% in an equal quantity or a ½ quantity of that of cobalt ion is added to the reaction solution. For example, when the concentration of $Co^{2+}$ ion is 2 mM, $H_2O_2$ is added to the reaction solution so that the final concentration of $H_2O_2$ is in a range from 1 mM to 2 mM.

Note that there may be cases in which apoferritin is denatured by addition of a hydrogen peroxide solution. Therefore, adding a salt is effective to stabilize apoferritin. As a salt, for example, $Na_2SO_4$ can be used. However, other salts may be also used. Moreover, when a cobalt-apoferritin

TABLE 1

| $Co^{2+}$ ion concentration | pH 8.0 | pH 8.2 | pH 8.3 | pH 8.4 | pH 8.6 | pH 8.8 |
|---|---|---|---|---|---|---|
| 2.0 mM | Poor | Poor | Poor | Fair | Fair | Fair |
| 2.5 mM | Not examined | Good | Good | Good | Not examined | Not examined |
| 3.0 mM | Good | Excellent | Excellent | Excellent | Good | Fair |
| 3.5 mM | Not examined | Excellent | Excellent | Excellent | Not examined | Not examined |
| 4.0 mM | Good | Excellent | Good | Good | Poor | Poor |
| 5.0 mM | Excellent | Excellent | Not examined | Poor | Poor | Poor |

Note that although HEPES is out of the range in which it can exhibit a high buffer capacity when the solution is in a pH range from about 8.0 to 8.8, the concentration of HEPES may be made to be at a high level. The HEPES concentration in the reaction solution may be at any level as long as the variation range of pH is sufficiently small, even though precipitates of cobalt hydroxide (CoO(OH)) appear. For example, when the concentration of cobalt ions in the reaction solution is 3 mM, a HEPES buffer solution containing HEPES at a concentration of 90 mM or more may be used.

The concentration of apoferritin in the reaction solution is adjusted to be in a range from 0.1 to 1 mg/ml (about 0.2-2 μM). More specifically, it is preferably about 0.5 mg/ml (1 μM).

The concentration of $Co^{2+}$ ion is adjusted according to the concentration of apoferritin. The $Co^{2+}$ ion concentration may be about 1000 to 5000 times more than that of the apoferritin concentration. More specifically, it is preferably about 2000 to 3000 more than that of the apoferritin concentration. Note that $Co^{2+}$ ions may be added at a higher concentration than the above-described level. If $Co^{2+}$ ions are added at a high concentration, CoO(OH) is formed vigorously outside of the holding portion of the apoferritin complex is produced, the existence of $Cl^-$ ions may be an obstacle to the production ($Cl^-$ ions stabilize $Co^{2+}$ ions to inhibit the formation of CoO(OH)). Therefore, it is preferable to use a salt not including Cl.

A salt may be added to the solution at a concentration of 10 mM or more. Test results also show that in the case of $Na_2SO_4$, it is sufficient for stabilization of apoferritin to add $Na_2SO_4$ at a concentration of about 30-150 mM.

The above-described conditions for the reaction solution will be shown in Table 2.

TABLE 2

|  | Apoferritin | $Co^{2+}$ ion | HEPES | $H_2O_2$ |
|---|---|---|---|---|
| Quantity ratio | 1 | 2000–5000 | 10000–100000 | 1000–5000 |
| Concentration | 0.5 mg/ml (1 μM) | 2 mM to 5 nM | 10 mM to 100 mM | 1 mM to 5 M |

It should be avoided that $Cl^-$ ions come into the reaction solution during the process steps for preparing the reaction solution. More preferably, oxygen is exhausted from the reaction solution by bubbling nitrogen or other means.

Under the above-described conditions, the color of the reaction solution is pink, i.e., a color that $Co^{2+}$ ions exhibit in Step St1.

In Step St2, when CoO(OH) is generated by the addition of a hydrogen peroxide solution, the color of the reaction solution turns to a color between brown and green, i.e., a color that $Co^{3+}$ exhibits. Measured by a spectrophotometer, CoO(OH) has become a hydroxide which has an absorption peak at around 350 nm.

Normally, if the reaction solution is reacted at room temperature under the above-described conditions, time required for the reaction is from several hours to several days. However, the temperature of the reaction solution may be increased to 40° C. to 70° C. to facilitate the reaction. By increasing the solution temperature, the reaction can be finished in several hours or over a night. Since apoferritin particles become unstable at a temperature over 70° C., it is preferable to increase the temperature of the reaction solution to a temperature ranging from room temperature to 70° C. More specifically, it is more preferable to increase the temperature of the reaction solution to 50-60° C. As another option, if thermophile apoferritin is used, the temperature may be increased to about 80-100° C. This is because the crystallinity of generated CoO(OH) under the above-described temperature conditions is improved in such a case.

Note that in this embodiment, $Na_2SO_4$ is added to the reaction solution so that the final concentration of $H_2O_2$ is 2 mM and the final concentration of $Na_2SO_4$ is 75 mM and the temperature of the reaction solution is increased to 50° C., in Step St2.

In general, a buffer solution should not influence a chemical substance in a solution. However, in the case of the HEPES buffer solution used in this embodiment, it is presumed that HEPES and $Co^{2+}$ ions interact with each other and then form $Co^{2+}$-HEPES associated pairs. The reaction solution then may be in an equilibrium state represented by the following chemical reaction formula 2.

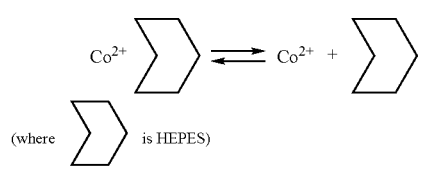

[Formula 2]

Figure 3:
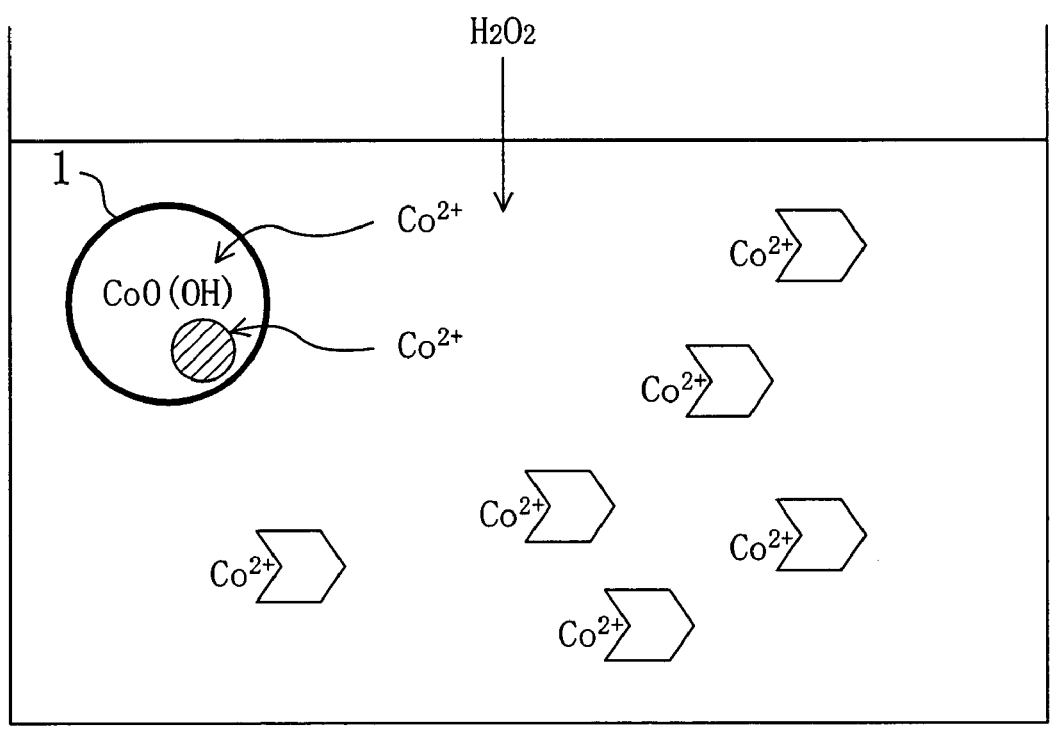
FIG. 3 is a schematic illustration of a state of a reaction solution.
Figure 3:

The state of the reaction solution then is schematically shown in FIG. 3.

As the chemical reaction formula 2 and FIG. 3 shows, a $Co^{2+}$-HEPES associated pair, a simple HEPES ion and a simple $Co^{2+}$ ion are present to make an equilibrium state.

Assume that used is a reaction solution including water instead of a HEPES buffer solution in Step St1. When a hydrogen peroxide solution is added to the reaction solution, $Co^{2+}$ ions immediately react, so that CoO(OH) which is a $Co^{3+}$ compound is formed, as shown in the chemical reaction formula 1. CoO(OH) is insoluble and thus immediately precipitates. As a result, all $Co^{2+}$ ions become CoO(OH) precipitates.

However, it is also presumed that in this embodiment, when a hydrogen peroxide solution is added, $H_2O_2$ can not oxidize the $Co^{2+}$-HEPES associated pairs which are of an associated form of a $Co^{2+}$ ion and HEPES. Therefore, very few $Co^{2+}$ ions existing in the solution are oxidized by $H_2O_2$ outside of apoferritin, and then become CoO(OH) precipitates.

In contrast, the holding portion 4 of the apoferritin 1 has a negative charge at around pH 8. Therefore, as shown in FIG. 3, the concentration of $Co^{2+}$ ion at around pH 8 is higher than that of the outside of the apoferritin 1. Accordingly, CoO(OH) is preferentially formed in the holding portion 4 of the apoferritin 1. Furthermore, contact catalysis occurs on the surface of CoO(OH) and therefore the reaction is accelerated rapidly in the holding portion 4.

Since $Co^{2+}$ ions become CoO(OH) precipitates due to the addition of $H_2O_2$, the number of $Co^{2+}$ ions in the whole solution is reduced. However, since the reaction represented by the chemical reaction formula 2 is chemically balanced, the $Co^{2+}$-HEPES associated pairs are dessociated and thus $Co^{2+}$ ions are supplied. Therefore, the concentration of $Co^{2+}$ ion in the reaction solution is low but can be maintained substantially constant.

As a result of the above-described mechanism, $Co^{2+}$ ions are supplied from the $Co^{2+}$-HEPES associated pairs to the apoferritin 1 and then concentrated by the negative charge of holding portion 4 of the apoferritin 1. Thus, the formation of CoO(OH) is facilitated in the holding portion 4 so that a cobalt-apoferritin complex is formed.

Next, operations subsequent to Step St2 will be described.

First, the reaction solution obtained in Step St2 is put into a vessel and is centrifuged at a speed of 3000 rpm for 15-30 minutes by a centrifugal separator such that precipitates are removed. Subsequently, a supernatant liquid obtained after the removal of the precipitates is further centrifuged at a speed of 10000 rpm for 30 minutes such that an unnecessary bulk material in which cobalt-apoferritin complexes are condensed is precipitated and then removed. At this time, cobalt-apoferritin complexes are dispersed in the supernatant liquid.

Next, the solvent of the supernatant is dialyzed to replace a HEPES buffer solution at pH 7.0 and of 100 mM with an NaCl solution of 150 mM. In this manner, another cobalt-apoferritin complex solution is obtained. It is not particularly necessary to adjust the pH of the solution here.

Subsequently, the cobalt-apoferritin complex solution is condensed by dialysis so that the concentration of cobalt-apoferritin complex with respect to the whole solution is an arbitrary concentration ranging from 1 to 10 mg/l. Thereafter, $CdSO_4$ is added to the solution so that the final concentration of $CdSO_4$ becomes 10 mM. In this manner, cobalt-apoferritin complexes are condensed.

Next, the cobalt-apoferritin complex solution is centrifuged at a speed of 3000 rpm for 20 minutes so that ferritin aggregates in the solution are precipitated. Thereafter, the solution is dialyzed such that buffering elements in the solution is replaced with a Tris buffer solution at pH 8.0 and of 10-50 containing NaCl of 150 mM.

Next, the cobalt-apoferritin solution is concentrated and then filtered using a gel filtration column to obtain cobalt-apoferritin complexes. Thereafter, the cobalt-apoferritin complexes are stored in a proper solution.

As has been described, in this embodiment, pH adjustment is performed using a buffer solution and thereby the pH of the apoferritin solution can be set at a desired level. Thus, it is possible to prevent the reaction represented by the chemical reaction formula 1 from proceeding in the reverse direction. Accordingly, elution of cobalt particles contained in the cobalt-apoferritin complexes into the solution can be prevented. Therefore, in this embodiment, a cobalt-apoferritin complex containing a cobalt particle having a uniform diameter can be obtained.

More specifically, NaOH is not used in this embodiment and thus apoferritin is not denatured. Therefore, it is possible to keep apoferritin being in the state of where it can exhibits its original characteristics, i.e., in the state where it can sufficiently hold cobalt particles.

Moreover, in the method for producing a cobalt-apoferritin complex according to this embodiment, $Co^{2+}$ ions become CoO(OH) precipitates due to the addition of $H_2O_2$ and therefore the number of $Co^{2+}$ ions in the whole solution is reduced. However, through the parallel reaction of the chemical reaction formula 2, the $Co^{2+}$-HEPES associated pairs are dessociated and $Co^{2+}$ ions are supplied. $Co^{2+}$ ions are condensed because of the negative charge of holding portion 4 of the apoferritin 1. In the holding portion 4, formation of CoO(OH) proceeds and cobalt-apoferritin complexes are formed. Accordingly, even when a reaction scale is increased to an industrial level, cobalt-apoferritin complexes can be formed only by adding an oxidizing agent without paying special attentions for uniformly dispersing the oxidizing agent (i.e., $H_2O_2$ in this embodiment). Therefore, in the method for producing a cobalt-apoferritin complex of this embodiment, the process steps can be performed in an industrial scale in a relatively simple manner.

Figure 4:
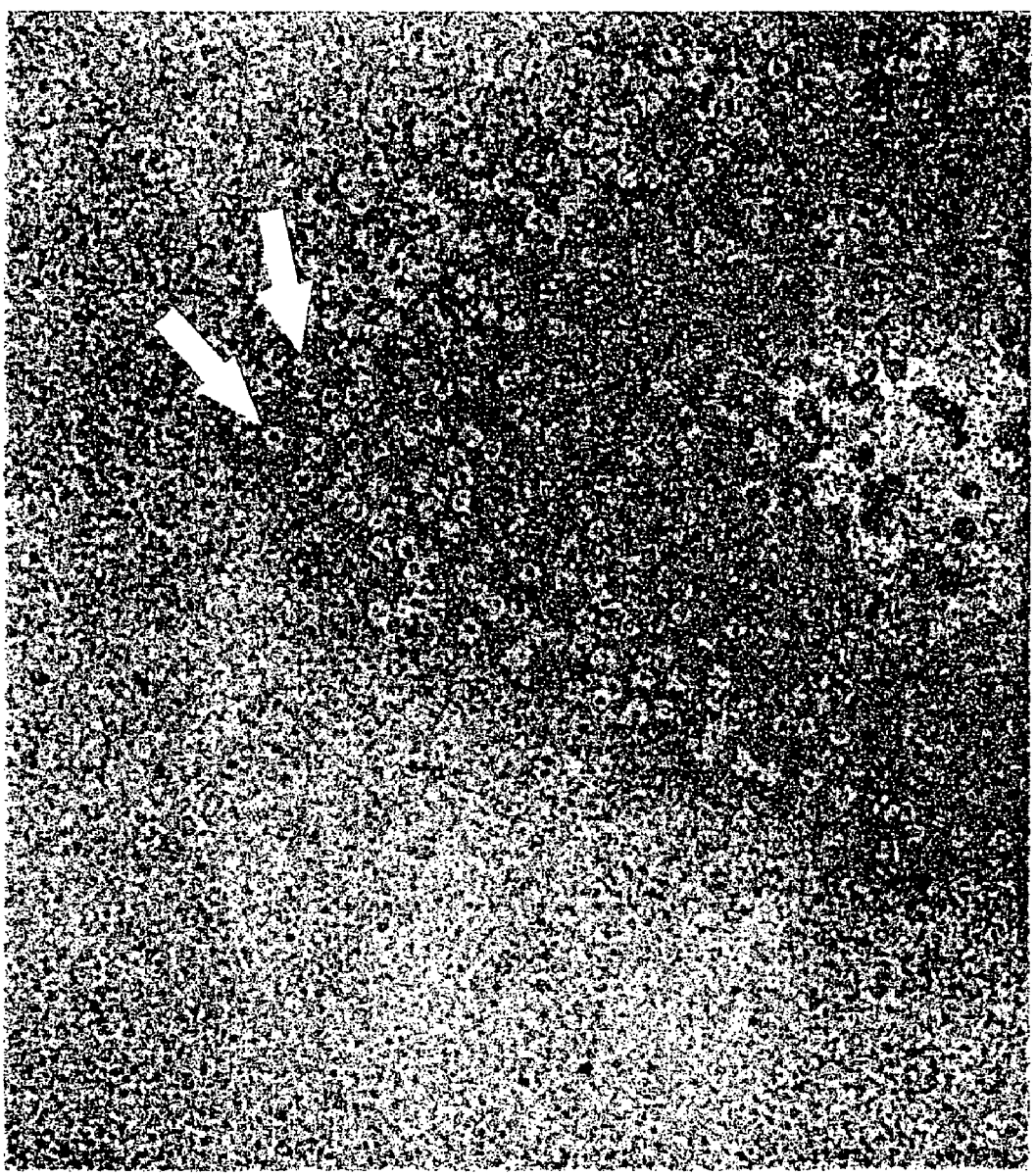
FIG. 4 is an electron micrograph of a cobalt-apoferritin complex obtained in Embodiment 1.

FIG. 4 is an electron micrograph of cobalt-apoferritin complexes obtained in this embodiment. In FIG. 4, typical cobalt-apoferritin complexes in which CoO(OH) is incorporated into (the holding portion of) apoferritin are pointed by the arrows.

Figure 5:
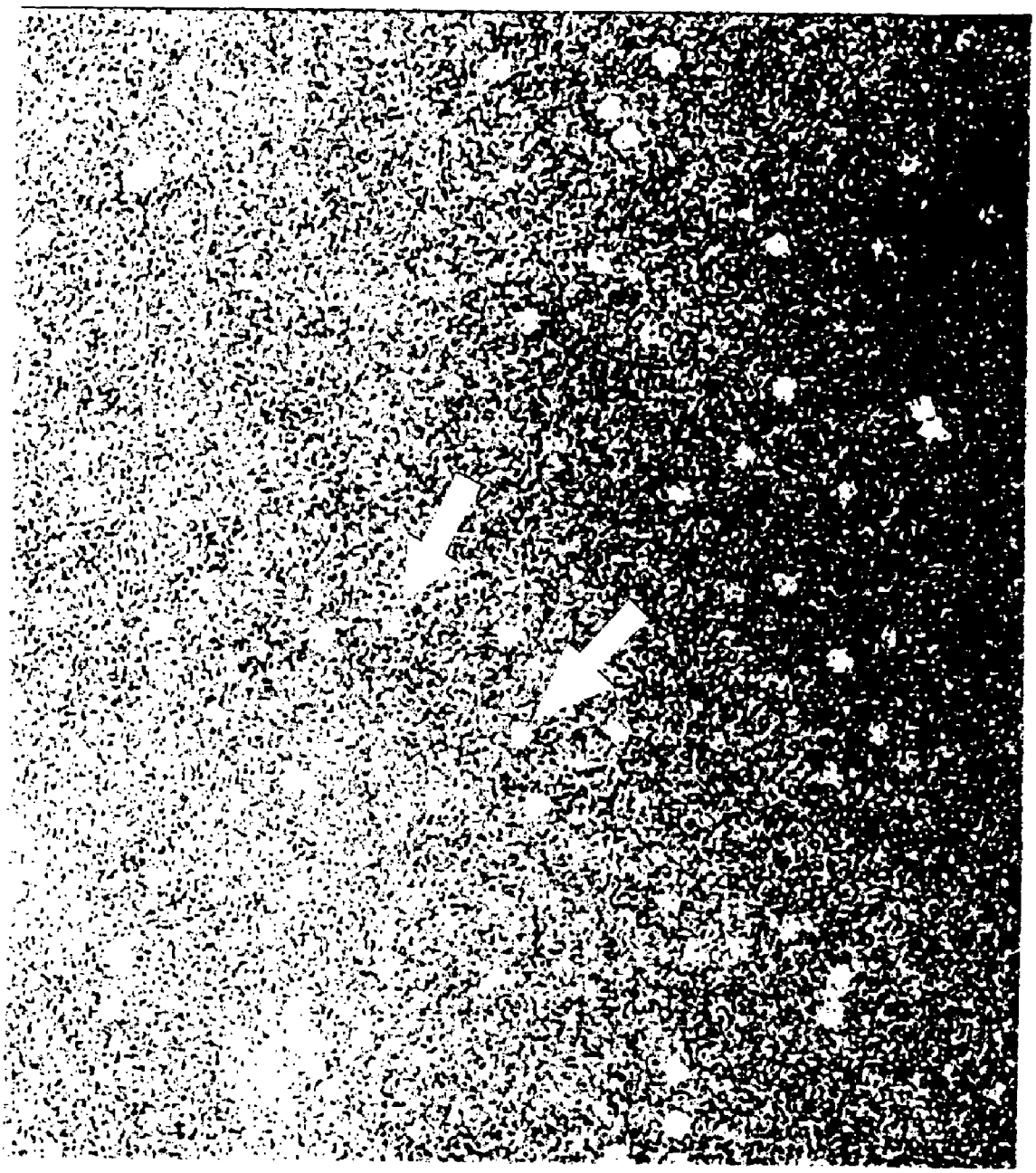
FIG. 5 is an electron micrograph of apoferritin obtained by the production method of Embodiment 1 in which a TAPS buffer solution is used instead of a HEPES buffer solution.

Meanwhile, FIG. 5 is an electron micrograph of apoferritin obtained by the production method of this embodiment in which a phosphoric acid buffer solution or a TAPS buffer solution is used instead of a HEPES buffer solution. Now, FIGS. 4 and 5 are compared. In FIG. 5, CoO(OH) is not incorporated into (the holding portion of) apoferritin as shown by typical ones pointed by the arrows. More specifically, if a phosphoric acid buffer solution is used, formation of CoO(OH) does not occur in a holding portion of apoferritin. The present inventors also confirmed that in some other buffer solution (e.g., a Tris buffer solution, a TAPS buffer solution and an acetic acid buffer solution), formation of CoO(OH) does not occur in a holding portion of apoferritin. The results suggest that all $Co^{2+}$ ions have become CoO(OH) precipitates outside of apoferritin in the solution and therefore they could not be condensed in the holding portion. That is to say, it seems that in the case of a TAPS buffer solution, a Tris buffer solution, a phosphoric acidbuffer solution, an acetic acid buffer solution or the like, there is no equilibrium state like one represented by the chemical reaction formula 2 and shown in FIG. 3 between $Co^{2+}$ ions and phosphoric acid, acetic acid, or Tris.

In view of the above described, it is presumed that HEPES used in this embodiment is a buffer and also functions as an associating agent which associates with $Co^{2+}$ ions. Therefore, if different reagents are used as a buffer solution and an associating agent, respectively, instead of the HEPES buffer solution used in this embodiment, a cobalt-apoferritin complex containing a cobalt particle having a uniform diameter can be obtained as in this embodiment. That is to say, if, for example, a TAPS buffer solution, a Tris buffer solution, a phosphoric acid buffer solution or the like is used as a buffer solution, and cyclodextrin, crown ether, calix arene or the like is used as an associating agent, the same effects as those of this embodiment can be achieved.

Moreover, in this embodiment, apoferritin is used as a protein for introducing cobalt. However, other proteins (e.g., Dps protein or CCMV protein) which can hold metal particles therein may be used instead of apoferritin.

Furthermore, in this embodiment, $H_2O_2$ is used as an oxidizing agent. However, other known oxidizing agents may be used. For example, $KMnO_4$, $K_2Cr_2O_7$, $HNO_3$, HClO, or NaClO may be used as an oxidizing agent instead of $H_2O_2$.

Embodiment 2

In this embodiment, a nonvolatile memory cell including as a floating gate a dot body which is formed by utilizing a cobalt-apoferritin complex produced in Embodiment 1 will be described.

FIGS. 6A through 6D are cross-sectional views illustrating respective process steps for fabricating a nonvolatile memory cell according to this embodiment.

Figure 6A:
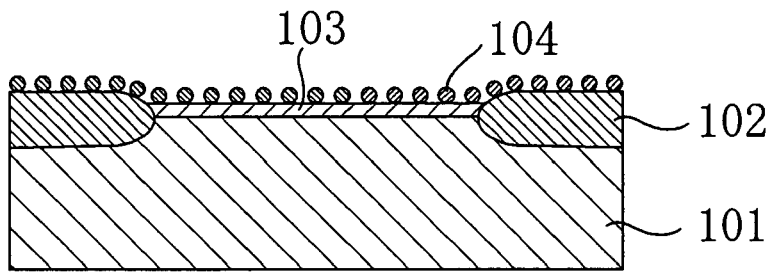
FIGS. 6A through 6D are cross-sectional views illustrating respective process steps for fabricating a nonvolatile memory cell according to this embodiment.

First, in the process step shown in FIG. 6A, an isolation oxide film 102 is formed on a p-type Si substrate 101 so as to surround an active region by LOCOS, and then a gate oxide film 103 that functions as a tunnel insulating film is formed on the substrate by thermal oxidation. Thereafter, dot bodies 104 each including a metal or semiconductor particle having a diameter of about 6 nm are formed on the substrate. The process step of forming the dot bodies 104 will be described later.

Figure 6B:
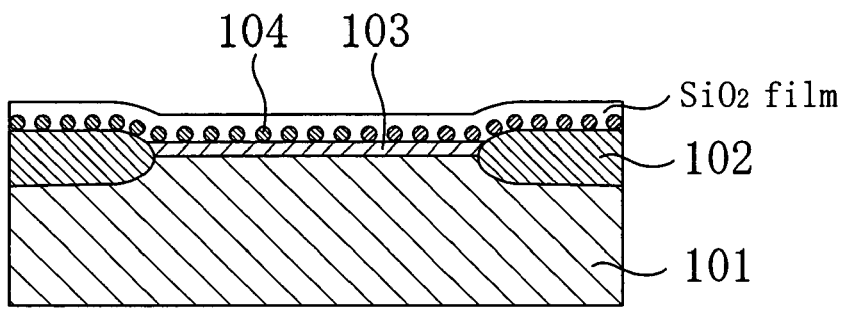

Next, in the process step shown in FIG. 6B, a $SiO_2$ film is deposited on the substrate by sputtering or CVD so that the dot bodies 104 are buried in the $SiO_2$ film.

Figure 6C:
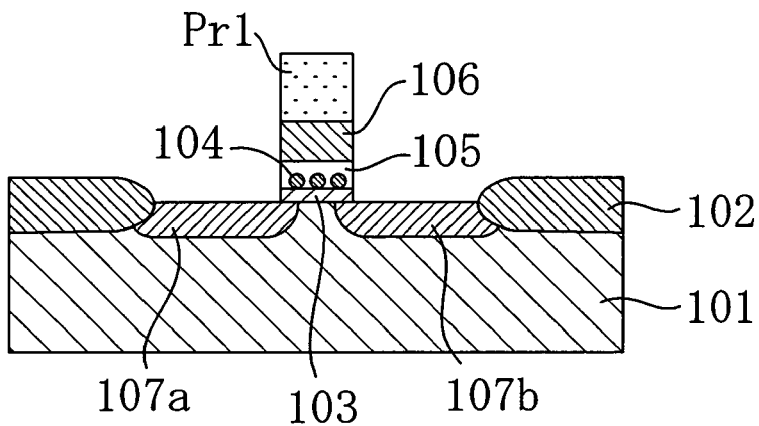

Next, in the process step shown in FIG. 6C, an Al film is deposited over the substrate. Subsequently, using a photoresist mask Pr1, the $SiO_2$ film and the Al film are patterned to form a silicon oxide film 105 that is to be an interelectrode insulating film and an Al electrode 106 that is to be a control gate electrode. At this point, part of the gate oxide film 103 which is not covered by the photoresist mask Pr1 is removed and thus some of the dot bodies 104 located thereon are also removed at the same time. Thereafter, using the photoresist mask and the Al electrode 106 as a mask, ions of an impurity are injected thereto, thereby forming first and second n-type doped layers 107a and 107b.

Figure 6D:
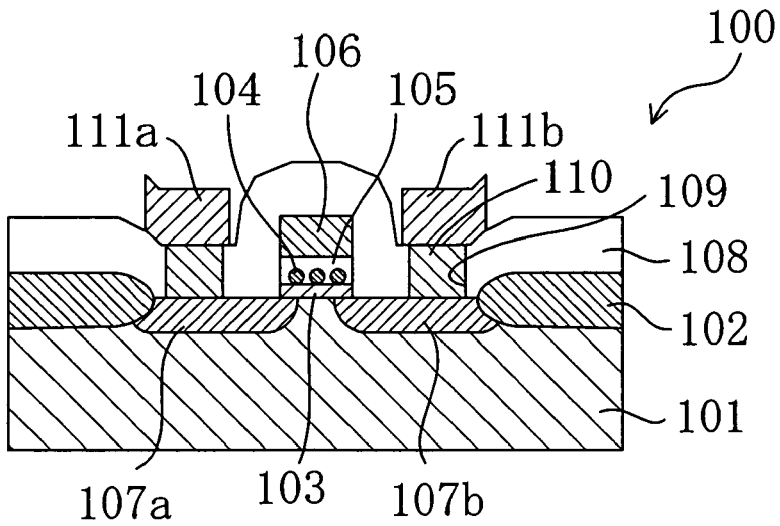

Then, in the process step shown in FIG. 6D, using known techniques, an interlevel insulating film 108 is formed, a contact hole 109 is formed so as to pass through to the interlevel insulating film 108, the contact hole 109 is filled with tungsten to form a tungsten plug 110, and then first and second aluminum interconnects 111a and 111b are formed.

In this embodiment, a p-type Si substrate is used. However, an n-type Si substrate may be used. Furthermore, a substrate formed of a GaAs compound semiconductor, some other compound semiconductor, or some other semiconductor may be used.

Next, in the process step shown in FIG. 6A, a technique for making the dot bodies 104 are formed on the substrate will be described with reference to FIGS. 7 and 8. Note that the present invention is not limited the following technique, but other known techniques may be also used.

Figure 7A:
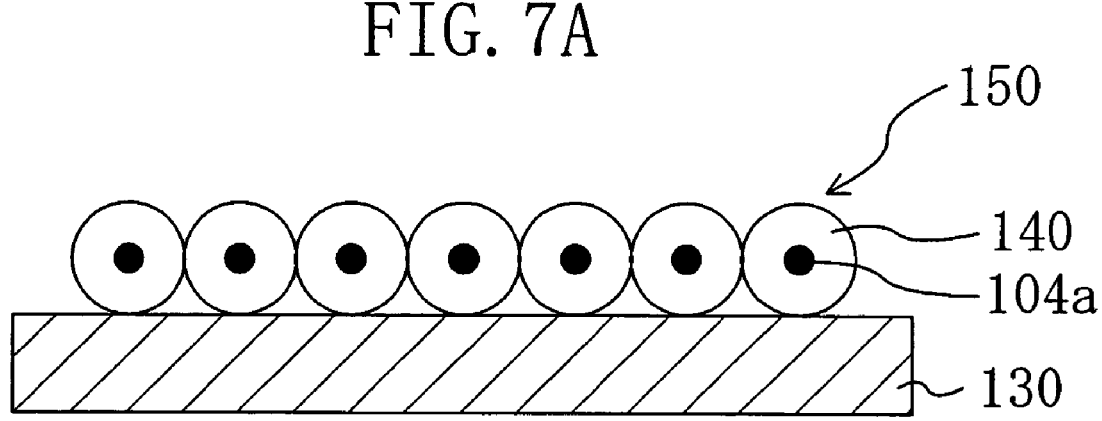
FIG. 7A through 7B show cross-sectional views illustrating the process step of arranging and immobilizing dots two-dimensionally on the surface of a substrate.

In the process step shown in FIG. 7A, cobalt-apoferritin complexes (which will be herein referred to as "complexes") 150 obtained in Embodiment 1 are prepared and the complexes 150 are placed on the surface of a substrate 130. In this manner, a complex film in which the complexes 150 are arranged at high density with high precision is formed on the substrate 130. Note that the substrate 130 is a substrate obtained in the process step shown in FIG. 6A, by forming on a p-type Si substrate 101 using LOCOS an isolation oxide film 102 which surround an active region and then forming on the substrate through thermal oxidation a gate oxide film 103 which functions as a tunnel insulating film. In the following description, the substrate 130 is a substrate obtained in the same manner as described here.

Figure 7B:
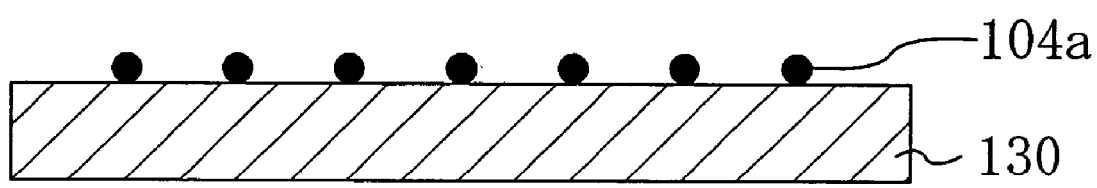

Next, in the process step shown in FIG. 7B, protein molecules 140 in the complexes 150 are removed so that only cobalt particles 104a are left. In this manner, the dot bodies 104 are formed on the substrate 130.

A technique for arranging the complexes 150 at high density with high precision on the surface of the substrate 130 performed in the process step shown in FIG. 7A, i.e., a method for arranging and immobilizing the complexes 150 two-dimensionally on the surface of the substrate 130 will be described. In this embodiment, the method disclosed in Japanese Patent Publication No. 11-45990 will be described hereinafter with reference to FIG. 8.

Figure 8A:
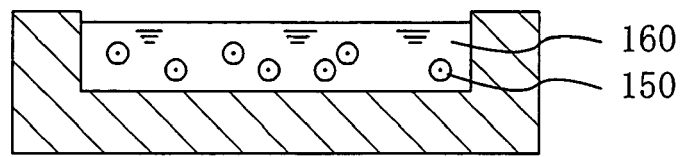
FIGS. 8A through 8E illustrate a technique for arranging and immobilizing complexes two-dimensionally on the surface of a substrate.

First, as shown in FIG. 8A, a liquid 160 in which complexes 150 are dispersed is prepared (i.e., a solution obtained by dispersing cobalt-apoferritin complexes in a solution obtained by mixing in equal volumes a phosphorus acid buffer solution having a concentration of 40 mM and pH 5.3 and a sodium chloride solution having a concentration of 40 mM is prepared in this embodiment).

Figure 8B:
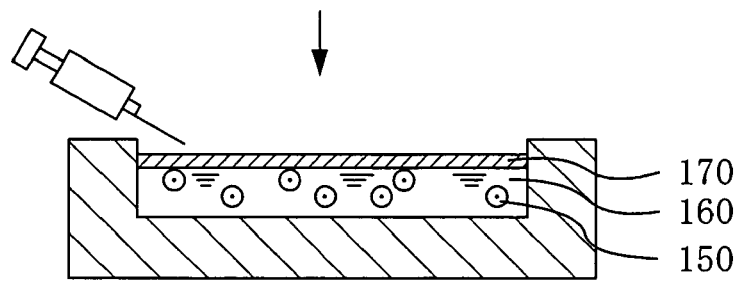

Subsequently, as shown in FIG. 8B, PBLH (poly-1-benzyl-L-histidine) is spread on the surface of the liquid 160 using an injector or the like. In this manner, a polypeptide film 170 of PBLH is formed on the surface of the liquid 160. At this time, the pH of the liquid 160 is adjusted.

Figure 8C:
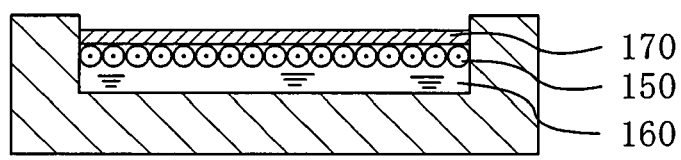

Next, as shown in FIG. 8C, the complexes 150 adhere to the polypeptide film 170 with the lapse of time and then two-dimensional crystals of the complexes 150 are formed. This is because the polypeptide film 170 has a positive charge while the complexes 150 have a negative charge.

Figure 8D:
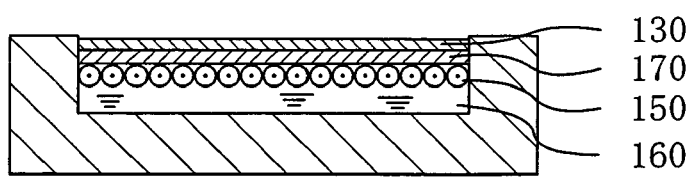

Next, as shown in FIG. 8D, a substrate 130 is mounted (floated) on the polypeptide film 170. In this manner, the polypeptide film 170 is adhered to the substrate 130.

Figure 8E:
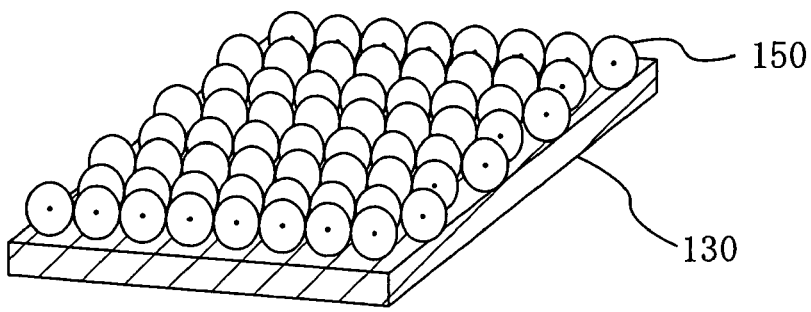

Next, as shown in FIG. 8E, the substrate 130 is taken out to obtain the substrate 130 to which the two-dimensional crystals of the complexes 150 adhere with the polypeptide film 170 interposed therebetween.

Next, further details of the process step shown in FIG. 7B will be described.

Because protein molecules are, in general, heat-sensitive, protein molecules of the complexes 150 are removed by heat treatment. For example, if the substrate 130 is left to stand for about 1 hour in an inert gas such as nitrogen gas at a temperature of 400-500° C., the protein molecules 140 and the polypeptide film 170 are burned out and then cobalt particles 104a are left on the substrate 130 as dot bodies 104 so as to be regularly arranged in a two-dimensional manner at high density with high precision.

In the above-described manner, as shown in FIG. 7B, it is possible to make the cobalt particles 104a held in the complexes 150 appear two-dimensionally on the substrate 130 and also form the dot bodies 104 regularly arranged at high density with high precision.

As shown in FIG. 6D, a memory cell 100 according to this embodiment is a nonvolatile memory cell which includes an MOS transistor (memory transistor) having an Al electrode 106 which functions as a control gate, first and second n-type doped layers 107a and 107b which function as a source and a drain, respectively, and utilizes changes in the threshold voltage of the memory transistor according to the amount of an electric charge stored in the dot bodies 104 each of which functions as a floating gate.

The nonvolatile memory cell can function as a binary memory. However, it is also possible to achieve a multivalued-data storing memory which can store three- or more-valued data by controlling not only the presence of charges to be stored in the dot bodies 104 but also the total amount of stored charges therein.

When data is erased, FN (Fowler-Nordheim) current passing through an oxide film or direct tunneling current is utilized.

When data is written, FN (Fowler-Nordheim) current passing through an oxide film or a direct tunneling current, or channel hot electron (CHF) injection is utilized In the nonvolatile memory cell of this embodiment, the floating gate is formed of cobalt particles having a diameter as small as they can function as quantum dots and thus the amount of charges to be stored is small. Therefore, the amount of current flowing when date is written or erased can be reduced, and thus a low-power consumption nonvolatile memory cell can be achieved.

Also, in the nonvolatile memory cell of this embodiment, the diameter of cobalt particles forming the floating gate is uniform. Thus, the characteristics of the cobalt particles when a charge is injected or removed are also uniform. Therefore, such an operation as injection or removal of a charge can be controlled in a simple manner.

Therefore, according to the present invention, a cobalt-protein complex containing a cobalt particle having a uniform diameter can be obtained.

A method for producing a cobalt-protein complex according to the present invention is applicable to fabrication of devices requiring hyperfine patterning, and more particularly applicable to fabrication of hyperfine electric devices such as a nonvolatile memory cell including a dot body as a floating gate.

What is claimed is:

1. A method for producing a cobalt-protein complex comprising:
   the step a) of preparing a solution including $Co^{2+}$ ions, a protein, and HEPES, and having a pH of not less than 8.0 and not more than 8.8; and
   a step b) of adding an oxidizing agent to the solution and thereby making the protein contain particles composed of cobalt,
   wherein the protein is apoferritin,
   the concentration of the $Co^{2+}$ ions is not less than 2.5 mM and not more than 5.0 mM,
   the pH of the solution is adjusted to be not less than 8.0 and not more than 8.8 when the concentration of the $Co^{2+}$ ions is not less than 2.5 mM and not more than 3.5 mM,
   the pH of the solution is adjusted to be not less than 8.0 and not more than 8.4 when the concentration of the $Co^{2+}$ ions is more than 3.5 mM and not more than 4.0 mM, and
   the pH of the solution is adjusted to be not less than 8.0 and not more than 8.2 when the concentration of the $Co^{2+}$ ions is more than 4.0 mM and not more than 5.0 mM.

2. The method for producing a cobalt-protein complex of claim 1, wherein the oxidizing agent is $H_2O_2$.

3. The method for producing a cobalt-protein complex of claim 1, wherein the step b) is performed at a temperature of 70° C. or less.

4. The method for producing a cobalt-protein complex of claim 1, wherein the particles composed of cobalt includes CoO(OH).

5. The method for producing a cobalt-protein complex of claim 1, wherein the step b) is performed at a temperature of not less that 40° C. and not more than 70° C.

6. The method for producing a cobalt-protein complex of claim 5, wherein the step b) is performed at a temperature of not less than 50° C. and not more than 60° C.

* * * * *